US012655457B2

(12) United States Patent
Zhu et al.

(10) Patent No.: US 12,655,457 B2
(45) Date of Patent: Jun. 16, 2026

(54) ALLULOSE 3-EPIMERASE MUTANT, ENGINEERED BACTERIUM EXPRESSING SAME, AND IMMOBILIZED ENZYME AND IMMOBILIZATION METHOD THEREOF

(71) Applicant: TIANJIN YEAHE BIOTECHNOLOGY CO., LTD., Tianjin (CN)

(72) Inventors: Yueming Zhu, Tianjin (CN); Peng Chen, Tianjin (CN); Yuanxia Sun, Tianjin (CN); Yan Zeng, Tianjin (CN); Jiangang Yang, Tianjin (CN); Yan Men, Tianjin (CN); Yanhe Ma, Tianjin (CN)

(73) Assignee: TIANJIN YEAHE BIOTECHNOLOGY CO., LTD., Tianjin (CN)

( * ) Notice: Subject to any disclaimer, the term of this patent is extended or adjusted under 35 U.S.C. 154(b) by 822 days.

(21) Appl. No.: 17/753,739

(22) PCT Filed: Dec. 15, 2020

(86) PCT No.: PCT/CN2020/136574
§ 371 (c)(1),
(2) Date: Mar. 13, 2022

(87) PCT Pub. No.: WO2021/244005
PCT Pub. Date: Dec. 9, 2021

(65) Prior Publication Data
US 2022/0340944 A1 Oct. 27, 2022

(30) Foreign Application Priority Data

Jun. 3, 2020 (CN) .......................... 202010496928.9
Sep. 18, 2020 (CN) ........................ 202010985171.X

(51) Int. Cl.
*C12P 19/02* (2006.01)
*C12N 1/20* (2006.01)
*C12N 9/90* (2006.01)
*C12N 15/75* (2006.01)
*C12P 19/24* (2006.01)

(52) U.S. Cl.
CPC ................ *C12P 19/02* (2013.01); *C12N 1/20* (2013.01); *C12N 9/90* (2013.01); *C12N 15/75* (2013.01); *C12P 19/24* (2013.01); *C12Y 501/03* (2013.01); *C12N 2800/101* (2013.01)

(58) Field of Classification Search
CPC .................................. C12N 9/90; C12P 19/24
See application file for complete search history.

(56) References Cited

FOREIGN PATENT DOCUMENTS

| | | | |
|---|---|---|---|
| CN | 103131721 A | 6/2013 | |
| CN | 103789377 A | 5/2014 | |
| CN | 103952358 A | 7/2014 | |
| CN | 102869783 B | 3/2016 | |
| CN | 105637089 A | 6/2016 | |
| CN | 106164265 A | 11/2016 | |
| CN | 104160023 B | 3/2017 | |
| CN | 106480005 A | 3/2017 | |
| CN | 108239633 A | 7/2018 | |
| CN | 108531527 A * | 9/2018 | |
| CN | 105602925 B | 1/2019 | |
| CN | 110079488 A | 8/2019 | |
| CN | 105602879 B | 9/2019 | |
| CN | 110438113 A | 11/2019 | |
| CN | 105637089 B * | 6/2021 | ............. A23L 29/30 |
| WO | 2015032761 A1 | 3/2015 | |
| WO | 2018116266 A1 | 6/2018 | |

OTHER PUBLICATIONS

Poyet et al. NCBI Accession # MZL35252, Direct Submission Submitted (Nov. 6, 2019) Biological Engineering, Massachusetts Institute of Technology, 77 Massachusetts Avenue, Cambridge, MA 02139, USA (Year: 2019).*
Li et al. J Chem Technol Biotechnol 2018; 93: pp. 350-357 (Year: 2018).*
Patel et al. Applied and Environmental Microbiology, Mar. 2020, vol. 86, Issue 5, pp. 1-14 (Year: 2020).*
Bosshart et al. ChemBioChem 2015, 16, pp. 592-601 (Year: 2015).*
Ward et al. NCBI Accession # ZP_04858451, Direct submission, Submitted (Mar. 20, 2009) Broad Institute of MIT and Harvard, Cambridge Center, Cambridge, MA 02142, USA (Year: 2009).*
Zhang et al. J. Agric. Food Chem. 2016, 64, 3386-3393 (Year: 2016).*
Zhu et al. Microb Cell Fact (2019) 18:59, pp. 1-10 (Year: 2019).*
Prabhu et al. Bioorganic & Medicinal Chemistry Letters 20 (2010) 4436-4439 (Year: 2010).*
Sugar phosphate isomerase/epimerase [*Ruminococcus* sp. AM54-14NS], Genbank accession No. RHP98822.1, Aug. 1, 2018; pp. 1-2.
Song, Lianming et al.; "A local screening method for biocatalysts"; Hebei Chemical Industry; vol. 32, No. 7; Jul. 2009; pp. 49-51.

(Continued)

*Primary Examiner* — Louise W Humphrey
*Assistant Examiner* — Jessica Faye Edwards
(74) *Attorney, Agent, or Firm* — NKL Law; Allen Xue

(57) ABSTRACT

An allulose 3-epimerase mutant, a genetically engineered bacterium expressing the mutant, and an immobilized allulose 3-epimerase enzyme and an immobilization method thereof are described. A high-throughput screening method is used to obtain an allulose 3-epimerase mutant efficiently expressed in a fermentation process, which can catalyze efficient conversion of fructose to D-allulose, providing an efficient production path for key enzymes required in a D-allulose production process. Additionally, the allulose 3-epimerase is bonded to an immobilizing resin to prepare an immobilized allulose 3-epimerase enzyme. The immobilized enzyme can be applied to batch or continuous reactions to catalyze efficient conversion of fructose to D-allulose.

12 Claims, 5 Drawing Sheets

Specification includes a Sequence Listing.

(56) References Cited

OTHER PUBLICATIONS

"Clostridium bolteae 3-epimerase protein, Seq ID 9."; Genbank accession No. XP002809604; Aug. 11, 2016.

"Treponema primitia D-psicose 3-epimerase mutant A229E/N264D, Seq ID 4."; Genbank accession No. XP002809605; Apr. 10, 2014.

Zhang W. et al.; "Improving the Thermostability and Catalytic Efficiency of the D-psicose 3-epimerase from Clostridium bolteae ATCC BAA-613 Using Site-Directed Mutagenesis"; Journal of Agricultural and Food Chemistry; vol. 64, No. 17; Apr. 22, 2016; ISSN: 0021-8561; pp. 3386-3393.

Choi, Jin-Geun et al.; "Improvement in the Thermostability of D-Psicose 3-Epimerase from Agrobacterium tumefaciens by Random and Site-Directed Mutagenesis"; Applied and Environmental Microbiology; vol. 77, No. 20; Oct. 15, 2011; ISSN: 0099-2240; pp. 7316-7320.

Zhu, Yueming et al.; "Overexpression of D-psicose 3-epimerase from *Ruminococcus* sp. in *Escherichia coli* and its potential application in D-psicose production"; Biotechnology Letters; vol. 34, No. 10; Jul. 4, 2012; ISSN: 1573-6776; pp. 1901-1906.

Lopez-Gallego, Fernando et al; "Enzyme Stabilization by Glutaraldehyde Crosslinking of Absorbed Proteins on Aminated Supports"; Journal of Biotechnology; vol. 119, No. 1; Sep. 22, 2005; ISSN: 0168-1656; pp. 70-75.

Zhu, Zhangliang et al., "Redesign of a novel D-allulose 3-epimerase from *Staphylococcus aureus* for thermostability and efficient biocatalytic production of D-allulose", Microbial Cell Factories, vol. 18, No. 1, Chapter 59, pp. 1-10. Mar. 25, 2019, No. 1-14.

\* cited by examiner

SEQUENCE LISTING

```
<160> NUMBER OF SEQ ID NOS: 1

<210> SEQ ID NO 1
<211> LENGTH: 291
<212> TYPE: PRT
<213> ORGANISM: Ruminococcus sp.

<400> SEQUENCE: 1

Met Lys Tyr Gly Ile Tyr Tyr Ala Tyr Trp Glu Lys Glu Trp Asn Gly
1               5                   10                  15

Asp Tyr Lys Tyr Tyr Ile Asp Lys Ile Ser Lys Leu Gly Phe Asp Ile
            20                  25                  30

Leu Glu Ile Ser Cys Gly Ala Phe Ser Asp Tyr Tyr Thr Lys Asp Gln
        35                  40                  45

Glu Leu Ile Asp Ile Gly Lys Tyr Ala Lys Glu Lys Gly Val Thr Leu
    50                  55                  60

Thr Ala Gly Tyr Gly Pro His Phe Asn Glu Ser Leu Ser Ser Ser Glu
65                  70                  75                  80

Pro Asn Thr Gln Lys Gln Ala Ile Ser Phe Trp Lys Glu Thr Leu Arg
                85                  90                  95

Lys Leu Lys Leu Met Asp Ile His Ile Val Gly Gly Ala Leu Tyr Gly
                100                 105                 110

Tyr Trp Pro Val Asp Tyr Ser Lys Pro Phe Asp Lys Lys Arg Asp Leu
            115                 120                 125

Glu Asn Ser Ile Lys Asn Met Lys Ile Ile Ser Gln Tyr Ala Glu Glu
    130                 135                 140

Tyr Asp Ile Met Met Gly Met Glu Val Leu Asn Arg Phe Glu Gly Tyr
145                 150                 155                 160

Met Leu Asn Thr Cys Asp Glu Ala Leu Ala Tyr Val Glu Glu Val Gly
                165                 170                 175

Ser Ser Asn Val Gly Val Met Leu Asp Thr Phe His Met Asn Ile Glu
            180                 185                 190

Glu Asp Asn Ile Ala Ala Ala Ile Arg Lys Ala Gly Asp Arg Leu Tyr
```

-continued

```
            195                 200                 205

His Phe His Ile Gly Glu Gly Asn Arg Lys Val Pro Gly Lys Gly Met
    210                 215                 220

Leu Pro Trp Asn Glu Ile Gly Gln Ala Leu Arg Asp Ile Asn Tyr Gln
225                 230                 235                 240

His Ala Ala Val Met Glu Pro Phe Val Met Gln Gly Gly Thr Val Gly
                245                 250                 255

His Asp Ile Lys Ile Trp Arg Asp Ile Ile Gly Asn Cys Ser Glu Val
                260                 265                 270

Thr Leu Asp Met Asp Ala Gln Ser Ala Leu His Phe Val Lys His Val
        275                 280                 285

Phe Glu Val
    290
```

ALLULOSE 3-EPIMERASE MUTANT, ENGINEERED BACTERIUM EXPRESSING SAME, AND IMMOBILIZED ENZYME AND IMMOBILIZATION METHOD THEREOF

CROSS-REFERENCE TO RELATED APPLICATIONS

This application is a U.S. national stage entry of PCT International Application No. PCT/CN2020/136574, filed Dec. 15, 2020, which claims priority to Chinese Patent Application No. 202010496928.9 filed with China National Intellectual Property Administration on Jun. 3, 2020 and entitled "ALLULOSE 3-EPIMERASE MUTANT, ENGINEERED BACTERIUM EXPRESSING SAME AND USE THEREOF" and Chinese Patent Application No. 202010985171.X filed with China National Intellectual Property Administration on Sep. 18, 2020 and entitled "IMMOBILIZED ENZYME OF ALLULOSE 3-EPIMERASE, IMMOBILIZATION METHOD THEREFOR AND USE THEREOF", the content of which are incorporated herein by reference in their entirety.

INCORPORATION OF SEQUENCE LISTING

This application contains a sequence listing submitted in Computer Readable Form (CRF). The CFR file containing the sequence listing entitled "PA150-0147 ST25.txt", which was created on Mar. 13, 2022, and is 3,046 bytes in size. The information in the sequence listing is incorporated herein by reference in its entirety.

TECHNICAL FIELD

The present invention relates to the field of industrial biology technology, in particular to an allulose 3-epimerase (psicose 3-epimerase) mutant, and further to a genetically engineered strain secreting and expressing allulose 3-epimerase, a construction method therefor and use of the engineered strain in producing an allulose 3-epimerase preparation by fermentation; in addition, the present invention further relates to an immobilized enzyme of the mutant, a preparation method therefor and use thereof in producing allulose.

BACKGROUND

D-allulose is a C3 epimer of D-fructose. It has a sweetness of 70% of that of sucrose while has a caloric value of only 0.2 cal/g. Besides, it has special physiological functions such as improving lipid metabolism and reducing postprandial glycemia, and has a texture and characteristic similar to sucrose. Therefore, it is an ideal substitute for sucrose. It is reported that allulose is a weak inhibitor of α-glucosidase, α-amylase, maltase and sucrase, and is capable of inhibiting the metabolism of starch and disaccharides into monosaccharides in the gastrointestinal tract and also inhibiting, through transport proteins in the intestinal tract, the absorption of glucose by the body. Therefore, allulose has potential hypoglycemic effects and thus can be used for reducing postprandial hyperglycemia in humans. Allulose can be used as a low-calorie sweetener in beverages, yogurt, ice cream, baked food and other high-calorie foods. After recognizing D-allulose as GRAS (general recognized as safe), the U.S. Food and Drug Administration (FDA) approved a draft guideline allowing food manufacturers to exclude allulose from the listing of total and added sugars on the nutrition and supplement facts labels on Apr. 16, 2019, drawing great attention to allulose on the market.

Allulose is found in very small amounts in nature and is also known as a functional "rare sugar". At present, allulose is mainly produced by enzymatic conversion, that is, converting the fructose substrate to allulose by allulose 3-epimerase or tagatose 3-epimerase. As the research proceeds, the protein structures of some important allulose 3-epimerase such as allulose 3-epimerase from *Agrobacterium tumefaciens* and tagatose 3-epimerase derived from *Pseudomonas cichorii* were analyzed. Based on the important information provided by the protein structures, researchers have also conducted directed evolution experiments on some key enzymes to improve their activity and stability, so that the enzymes can be more suitable for industrial production.

The high-efficiency enzyme production process is another important factor determining whether or not such enzymes can be actually applied to industrial production. Researchers construct engineered strains heterologously expressing allulose 3-epimerase by using host bacteria such as *E. coli, B. subtilis* and *C. glutamicum* as starting strains. *B. subtilis* is an ideal host bacterium for producing such key enzymes by fermentation due to its high-efficiency protein expression and secretion function. Chinese Patent CN105602925B confirms that D-allulose 3-epimerase from *Ruminococcus* sp. (RDPE) is efficiently secreted outside *B. subtilis* through a non-classical secretion pathway. Due to such secretion properties of RDPE, the cost of enzyme production by fermentation can be greatly reduced, thereby reducing the production cost of the finished product allulose. Chinese Patent CN105602879B constructs an engineered *B. subtilis* strain capable of efficiently secreting RDPE. However, it is still necessary to develop an allulose 3-epimerase mutant that has high catalytic activity and great stability and can be more easily produced by fermentation.

In addition, immobilized enzymes have improved reusability and durability of enzymes and thus are more suitable for a continuous production process. Therefore, they are one of the key factors in further reducing the production cost of allulose. Besides, compared to using free enzymes, using immobilized enzymes can prevent other components in the enzyme extracts from being incorporated into the product, thereby simplifying the purification process of the product. Granted Patents CN102869783B and CN104160023B of CJ Cheiljedang Corporation discloses an immobilization method for engineered strains producing allulose 3-epimerase and continuous production of allulose by using the immobilized cells. In both the two patents, enzyme-producing engineered bacteria are immobilized by being entrapped in calcium alginate, extending the usage period of immobilized cells. However, the greatest defect lies in the fact that immobilization by entrapment enables only weak binding of enzymes or cells to carriers, which may cause leakage of the enzymes or cells. In addition, calcium alginate microspheres are complicated to prepare and have poor hardness, which is unfavorable for their long-term use. Therefore, it is still necessary to develop an enzyme immobilization process that is more suitable for industrial production of allulose 3-epimerase so as to greatly improve the reusability and durability of the immobilized enzyme and thus to reduce the production cost of allulose.

SUMMARY

The present invention provides an allulose 3-epimerase mutant, and further relates to a genetically engineered strain secreting and expressing allulose 3-epimerase, a construction method therefor and use of the engineered strain in producing an allulose 3-epimerase preparation by fermentation. In addition, the present invention further provides an immobilized enzyme of the allulose 3-epimerase (including wild-type enzymes, mutants or modified enzymes thereof) and a preparation method therefor. With this method, simple, high-efficiency and low-cost immobilization of allulose 3-epimerase can be achieved, thereby greatly improving the reusability and durability of the allulose 3-epimerase mutant.

The present invention adopts the following technical solutions:

In a first aspect, the present invention provides an allulose 3-epimerase (RDPE) mutant having activity for catalyzing epimerization of D-fructose to D-allulose, wherein an amino acid sequence of the mutant comprises a mutation of an amino acid residue corresponding to at least one of sites S36, Y44, D117, F157, C165, I196, Q251 and I265 of SEQ ID NO: 1.

According to an embodiment of the present invention, the amino acid sequence of the mutant comprises mutations of amino acid residues at any two of sites S36, Y44, D117, F157, C165, I196, Q251 and I265. In one embodiment, the amino acid sequence of the mutant comprises mutations at the above two sites, and at least one of the mutation sites is any one of sites F157, C165, Q251 and I265; preferably, one of the mutation sites of the amino acid sequence of the mutant is site F157, and the other mutation site is any one of sites C165, Q251 and I265. In yet another embodiment, the amino acid sequence of the mutant comprises mutations at the following two sites: Y44/F157, Y44/I196, D117/I196, F157/C165A, F157/Q251, F157/I265 or I196/Q251.

According to an embodiment of the present invention, the amino acid sequence of the mutant comprises mutations of amino acid residues at any three of sites S36, Y44, D117, F157, C165, I196, Q251 and I265. In one embodiment, the amino acid sequence of the mutant comprises mutations at sites F157/C165, and a mutation at any one of sites S36, Y44, D117, I196, Q251 and I265; preferably, the amino acid sequence of the mutant comprises mutations at sites F157/C165/I196 or F157/C165/Q251.

According to an embodiment of the present invention, the mutation of the amino acid residue at at least one of sites S36, Y44, D117, F157, C165, I196, Q251 and I265 is a substitution of a residue at at least one selected from sites S36N, Y44A, D117H, F157Y, C165A, I196F, Q251T and I265L. In one embodiment, the amino acid sequence of the mutant comprises a mutation at site F157Y; in one embodiment, the amino acid sequence of the mutant comprises any one of mutation site combinations Y44A/F157Y, Y44A/I196F, D117H/I196F, F157Y/C165A, F157Y/Q251T, F157Y/I265L and I196F/Q251T, preferably F157Y/C165A. In one embodiment, the amino acid sequence of the mutant comprises any one of mutation site combinations F157Y/C165A/S36N, F157Y/C165A/Y44A, F157Y/C165A/D117H, F157Y/C165A/I196F, F157Y/C165A/Q251T and F157Y/C165A/I265L, preferably F157Y/C165A/I196F or F157Y/C165A/Q251T.

According to an embodiment of the present invention, the mutant has no less than 70% homology, such as no less than 80% homology, further such as no less than 90%, no less than 95% or no less than 98% homology to the amino acid sequence set forth in SEQ ID NO: 1.

In a second aspect, the present invention also provides a nucleic acid encoding the above allulose 3-epimerase mutant.

In a third aspect, the present invention also provides a genetically engineered bacterium expressing the above allulose 3-epimerase mutant and comprising a nucleic acid encoding the allulose 3-epimerase mutant.

According to an embodiment of the present invention, the genetically engineered bacterium is a recombinant strain obtained by linking the nucleic acid to a vector to obtain a recombinant vector and then introducing the recombinant vector into a host bacterium.

According to an embodiment of the present invention, the host bacterium is any one selected from *E. coli, B. subtilis, C. glutamicum, Lactobacillus* and *Saccharomyces*, for example, may be selected from *B. subtilis* such as 168, WB600, WB800, WB800N, 1A751, FZB24 and SCK6, or from *E. coli* such as BL21(DE3), BL21(DE3) pLysS, Rosetta (DE3), EndoToxin-Free BL21(DE3), BL21 trxB (DE3) and JM109.

According to an embodiment of the present invention, the vector may be selected from vectors containing a *B. subtilis* replicon repB, for example, from any one of pHP13-43, pHT43, pHT304, pMK3, pMK4, pHCMC04, pHCMC05, pMA5, pHY300PLK and pYH-P43. Preferably, the vector is selected from a *B. subtilis* expression vector pNWP43N containing a constitutive expression promoter P43.

According to an embodiment of the present invention, the nucleic acid is linked to the vector using ligase or by PCR recombination to form a recombinant vector.

According to an embodiment of the present invention, the genetically engineered bacterium expresses an allulose 3-epimerase mutant.

In a fourth aspect, the present invention also provides a construction method for the above genetically engineered bacterium, comprising steps of linking the nucleic acid to a vector to obtain a recombinant vector and then introducing the recombinant vector into a host bacterium to obtain a recombinant strain.

In a fifth aspect, the present invention provides use of the genetically engineered bacterium in preparing an allulose 3-epimerase mutant.

In a sixth aspect, the present invention further provides a preparation method for an allulose 3-epimerase mutant, comprising a step of culturing the genetically engineered bacterium so as to allow the bacterium to express a nucleic acid encoding the allulose 3-epimerase mutant.

According to an embodiment of the present invention, the culturing is performed at a temperature of 35-40° C., preferably 37° C. for a duration of 24-72 h, preferably 48 h.

According to an embodiment of the present invention, the culturing is performed with stirring or shaking, for example, stirring at a rate of 100-1000 rpm, preferably 300-500 rpm.

According to an embodiment of the present invention, the preparation method also comprises a step of isolating the allulose 3-epimerase mutant from the culture.

In a seventh aspect, the present invention also provides use of the allulose 3-epimerase mutant in preparing D-allulose, wherein the mutant performs catalysis on the fructose substrate.

In an eighth aspect, the present invention also provides a production method for D-allulose, comprising contacting the allulose 3-epimerase mutant with fructose for catalysis.

According to an embodiment of the present invention, the catalysis is performed at a temperature of 40-80° C.; and the reaction system has a fructose concentration of 20-80% (w/v), for example, 50% (w/v).

In one embodiment, the production method for D-allulose comprises steps of adding fructose to a medium, culturing the genetically engineered bacterium of the invention and isolating D-allulose from the culture.

In yet another preferred embodiment, the production method for D-allulose comprises steps of culturing the genetically engineered bacterium of the invention so as to allow the bacterium to express a nucleic acid encoding the allulose 3-epimerase mutant, isolating the allulose 3-epimerase mutant from the culture and adding the isolated allulose 3-epimerase mutant to fructose for catalysis and thus to obtain D-allulose.

In a ninth aspect, the present invention also provides a screening method for a high-activity allulose 3-epimerase mutant, comprising steps of:

(1) establishing a mutant library, and constructing, culturing and isolating a strain;

(2) adding fructose to start a reaction;

(3) adding ribitol dehydrogenase (KRDH) and coenzyme NADH to start a second round of reaction and thus to obtain a reaction liquid; and (4) detecting changes in absorbance of the reaction liquid at 340 nm to identify a mutant with high catalytic activity.

In step (4), the more obvious the decrease in absorbance is, the more the amount of D-allulose generated is, indicating that the mutant has a higher catalytic activity.

The screening method according to the present invention further comprises a step of determining the content of D-allulose in the reaction liquid by high performance liquid chromatography for re-screening.

In a tenth aspect, the present invention also provides the above immobilized enzyme of allulose 3-epimerase, wherein the immobilized enzyme is obtained by binding an allulose 3-epimerase from *Ruminococcus* sp. and/or a mutant thereof and/or a molecularly-modified zymoprotein thereof (also referred to as "modified enzyme") to an immobilization resin.

According to an embodiment of the present invention, the enzyme immobilized in the immobilized enzyme of allulose 3-epimerase is allulose 3-epimerase from *Ruminococcus* sp. or a mutant thereof, the enzyme comprising an amino acid sequence having at least 60%, at least 70%, at least 80%, at least 85%, at least 90%, at least 95% or 100% identity to SEQ ID NO: 1.

According to an embodiment of the present invention, the enzyme immobilized in the immobilized enzyme of allulose 3-epimerase is the allulose 3-epimerase mutant described in the first aspect, or an allulose 3-epimerase mutant expressed by the genetically engineered bacterium described in the third aspect.

According to an embodiment of the present invention, the allulose 3-epimerase or the mutant thereof immobilized in the immobilized enzyme of allulose 3-epimerase is obtained by culturing an engineered strain carrying a gene encoding the enzyme or the mutant thereof by fermentation, wherein the engineered strain may be the genetically engineered bacterium expressing the allulose 3-epimerase mutant in the third aspect, or an engineered strain of *E. coli* or *B. subtilis* carrying a gene encoding allulose 3-epimerase.

According to an embodiment of the present invention, the carrier of the immobilized enzyme of allulose 3-epimerase is a slightly basic macroporous resin capable of forming a covalent bond with allulose 3-epimerase without compromising the enzyme activity, wherein the macroporous resin may be of an epoxy type or an amino type, but is not limited to these two types.

According to an embodiment of the present invention, the enzyme immobilized in the immobilized enzyme of allulose 3-epimerase is a modified enzyme of allulose 3-epimerase from *Ruminococcus* sp., wherein by introducing more basic amino acids, the covalent bonding between the enzyme and an epoxy group carrier is improved without changing the enzyme activity, thereby enhancing the immobilization effect and improving the immobilization efficiency; for example, in the modified enzyme, an AKAKAKAKAK tag is added to a carboxyl terminal of allulose 3-epimerase, and the immobilization efficiency is greatly improved through crosslinking between free amino groups in lysine and epoxy groups in resin.

According to an embodiment of the present invention, the immobilization resin may be a macroporous resin, such as an epoxy macroporous resin or an amino macroporous resin. Specific examples of the immobilization resin may include ES-1, ES-103, ES-108, ESR-1, ESR-2, ESQ-1, LX-1000HA, LX-1000EPN, LX-1000EPHA and the like.

In an eleventh aspect, the present invention also provides a preparation method for the immobilized enzyme of allulose 3-epimerase, comprising specific steps of:

(1) resin activation: activating a macroporous resin in a potassium phosphate buffer with a pH of 7.5-8.0;

(2) preparation of enzyme: preparing an enzyme extract by fermentation with an engineered bacterium heterogeneously expressing allulose 3-epimerase and/or a mutant thereof and/or a modified enzyme; preferably, the engineered bacterium may be *E. coli* or *B. subtilis*, or the genetically engineered bacterium in the third aspect;

(3) immobilization: adding the activated resin to the enzyme extract of allulose 3-epimerase and/or the mutant thereof and/or the modified enzyme for immobilization, preferably, at a temperature of 20-40° C. for a duration of 12-24 h; and (4) crosslinking: crosslinking the immobilized enzyme with a 0.2-0.5% glutaraldehyde solution, washing and draining off water to obtain the immobilized enzyme of allulose 3-epimerase.

According to an embodiment of the present invention, the resin in step (1) may be a macroporous resin, such as an epoxy macroporous resin or an amino macroporous resin. Specific examples of the immobilization resin may include ES-1, ES-103, ES-108, ESR-1, ESR-2, ESQ-1, LX-1000HA, LX-1000EPN, LX-1000EPHA and the like.

In a twelfth aspect, the present invention also provides a preparation method for an immobilized enzyme of the above allulose 3-epimerase mutant, comprising specific steps of:

(1) resin activation: activating a macroporous resin in a buffer;

(2) preparation of enzyme: preparing an enzyme extract by fermentation with the above genetically engineered bacterium expressing the allulose 3-epimerase mutant;

(3) immobilization: adding the activated resin to the enzyme extract of the allulose 3-epimerase mutant for immobilization; and (4) crosslinking: crosslinking the immobilized enzyme with a crosslinking reagent to obtain the immobilized enzyme of allulose 3-epimerase.

According to an embodiment of the present invention, the resin in step (1) may be a macroporous resin, such as an epoxy macroporous resin or an amino macroporous resin. Specific examples of the immobilization resin may include ES-1, ES-103, ES-108, ESR-1, ESR-2, ESQ-1, LX-1000HA, LX-1000EPN, LX-1000EPHA and the like.

According to an embodiment of the present invention, the buffer in step (1) may be a potassium phosphate buffer, for example, a potassium phosphate buffer with a pH of 7.5-8.0.

According to an embodiment of the present invention, the immobilization in step (3) may be performed at a temperature of 20-40° C. for a duration of 12-24 h.

According to an embodiment of the present invention, the crosslinking reagent in step (4) includes, but is not limited to, glutaraldehyde, glyoxal and the like. For example, the immobilized enzyme may be crosslinked with a 0.2-0.5% glutaraldehyde solution.

In a thirteenth aspect, the present invention also provides specific use of the immobilized enzyme of allulose 3-epimerase in producing allulose. Preferably, the immobilized enzyme performs catalysis on the fructose substrate.

According to an embodiment of the present invention, the immobilized enzyme of allulose 3-epimerase is capable of converting fructose to allulose, wherein the starting material has a fructose concentration of 20-75% (w/v), and may be a pure fructose solution, or mixed syrup containing fructose (for example, high-fructose syrup) or plant extracts containing fructose (for example, fruit juice).

According to an embodiment of the present invention, the conversion reaction of fructose to allulose by the immobilized enzyme of allulose 3-epimerase is conducted at a temperature of 40-70° C.; the reaction at low temperature can improve the reusability or durability of the immobilized enzyme, and the reaction at high temperature facilitates the improvement in the conversion rate.

According to an embodiment of the present invention, to the reaction system in which fructose is converted to allulose by the immobilized enzyme of allulose 3-epimerase is added 0.2-2.0 mM $Mn^{2+}$ or Co'; the addition of metal ions facilitates the improvement in the reusability or durability of the immobilized enzyme.

According to an embodiment of the present invention, the conversion reaction of fructose to allulose by the immobilized enzyme of allulose 3-epimerase may be conducted in a batch or continuous manner.

In a fourteenth aspect, the present invention also provides a production method for D-allulose, comprising contacting the immobilized enzyme of allulose 3-epimerase with fructose or a fructose-containing starting material for catalysis.

According to an embodiment of the present invention, the fructose-containing starting material has a fructose concentration of 20-75% (w/v), and may be a pure fructose solution, or mixed syrup containing fructose (for example, high-fructose syrup) or plant extracts containing fructose (for example, fruit juice).

According to an embodiment of the present invention, the catalysis is performed at a temperature of 40-70° C.

According to an embodiment of the present invention, the production method for D-allulose comprises a step of adding 0.2-2.0 mM $Mn^{2+}$ or $Co^{2+}$ to the reaction system.

According to an embodiment of the present invention, the production method for D-allulose may be implemented in a batch or continuous manner.

Beneficial Effects

In the present invention, a high-throughput screening method for mutants is constructed according to the catalytic properties of allulose 3-epimerase, a batch of allulose 3-epimerase mutants are identified, and the mutants have significantly improved specific enzyme activity, thermostability and heterologous expression levels compared to a wild type and capable of being efficiently expressed in *E. coli* and *B. subtilis*. Therefore, the present invention also provides a genetically engineered bacterium capable of secreting and expressing the enzyme. The activity of allulose 3-epimerase in fermentation broth of the genetically engineered bacterium can reach 1436 U/mL, and the efficient production of the key enzyme required in the production of D-allulose is achieved, significantly reducing the production cost of allulose. The genetically engineered bacteria have a wide application prospect.

In addition, the present invention also develops an immobilization method for allulose 3-epimerase (including a mutant or a modified enzyme thereof) to obtain an immobilized enzyme having significantly improved thermostability compared to free enzymes. The immobilized enzyme of allulose 3-epimerase can be used for producing allulose by taking fructose or various substrates rich in fructose as a starting material, and the conversion can be conducted in a batch or continuous manner.

The immobilization method greatly improves the reusability or durability of the enzyme, reduces the production cost and has a wide application prospect. In the immobilization method of the invention, a fermented crude enzyme extract is directly used for immobilization, thereby omitting the purification step in which RDPE mutant protein is extracted from the fermentation broth, reducing the cost and improving the immobilization efficiency of the target protein due to fewer protein impurities contained in the fermented crude enzyme extract.

DETAILED DESCRIPTION

Figure 1:
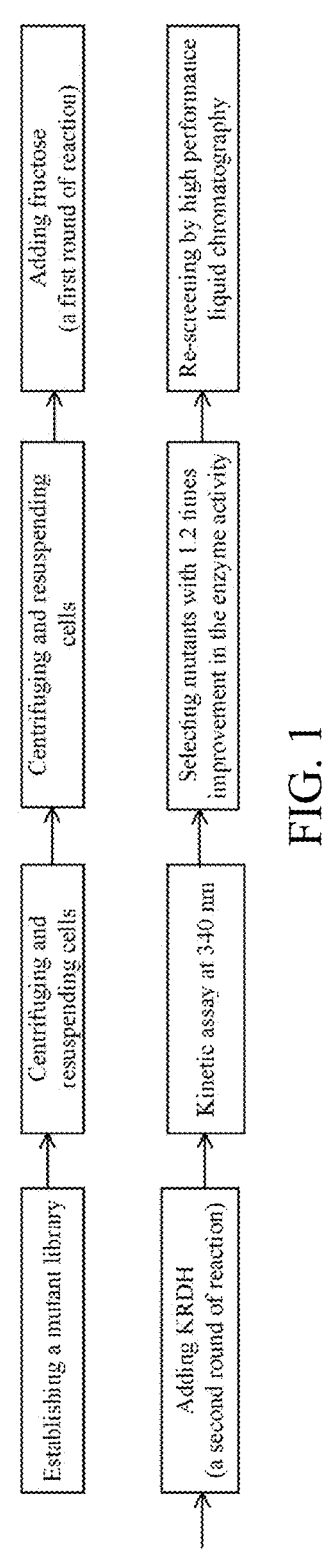
FIG. 1 is a schematic diagram of a high-throughput screening strategy for mutants.

The amino acids in the present invention are represented by single-letters or three-letter codes as follows: A: Ala (alanine); R: Arg (arginine); N: Asn (asparagine); D: Asp (aspartic acid); C: Cys (cysteine); Q: Gln (glutamine); E: Glu (glutamic acid); G: Gly (glycine); H: His (histidine); I: Ile (isoleucine); L: Leu (leucine); K: Lys (lysine); M: Met (methionine); F: Phe (phenylalanine); P: Pro (proline); S: Ser (serine); T: Thr (threonine); W: Trp (tryptophan); Y: Tyr (tyrosine); and V: Val (valine).

In the present invention, "homology" has the conventional meaning in the art and refers to "identity" between two nucleic acid or amino acid sequences, and the homology percentage refers to the statistical percentage of the identical nucleotides or amino acid residues between the two sequences to be compared obtained after best alignment, the differences between the two sequences being randomly distributed over their entire length.

In the present invention, the variants are described by their mutations at specific residues, the sites of which are determined by alignment with the wild-type enzyme sequence SEQ ID NO: 1 or by reference to the enzyme sequence SEQ ID NO: 1. In the context of the present invention, it also relates to any variant carrying the same mutations at functionally equivalent residues.

In the present invention, the terms "primer" and "primer strand" are used interchangeably and refer to initial nucleic acid fragments, typically RNA oligonucleotides, DNA oligonucleotides or chimeric sequences that are complementary to all or some binding sites of a target nucleic acid molecule. The primer strand may include natural, synthetic or modified nucleotides. The minimum length of the primer is the minimum length required to form a stable duplex under the reaction conditions for nucleic acid amplification.

In the present invention, the terms "mutant" and "variant", as well as the terms "modification" or "mutation", are used interchangeably; these terms mean that relative to the amino acids of wild-type proteins such as allulose 3-epimerase of the wild-type sequence SEQ ID NO: 1 from *Ruminococcus* sp., or derived on the basis of such an enzyme, a protein has a sequence comprising alterations, namely substitutions, insertions and/or deletions, at one or more sites while still retains its activity. Mutants can be obtained by various techniques known in the art. Exemplary techniques for modifying a DNA sequence encoding a wild-type protein include, but are not limited to, site-directed mutagenesis, random mutagenesis and construction of synthetic oligonucleotides. The modified DNA sequence is then allowed to express in a host bacterium to obtain mutants having substitutions, insertions and/or deletions of amino acid sequences. In the present invention, the expressions "the mutant comprises mutations at sites . . . " and "the amino acid sequence of the mutant comprises mutations at sites . . . " have the same meaning indicating that substitutions, insertions and/or deletions occur at specific sites of the amino acid sequence of the mutant protein. The term "substitution" with respect to an amino acid site or residue means that the amino acid at a specific site has been replaced by another amino acid. The substitution may be conservative or non-conservative.

The term "corresponding to" used herein has the meaning commonly understood by those of ordinary skill in the art. Specifically, the term "corresponding to" refers to a site in a sequence corresponding to a specified site in another sequence after alignment of the two sequences by homology or sequence identity. Therefore, for example, in terms of "an amino acid residue corresponding to site 40 of the amino acid sequence set forth in SEQ ID NO: 1", if a 6×His tag is added to one end of any of the amino acid sequences set forth in SEQ ID NO:1, it may be site 46 in the resultant mutant that corresponds to site 40 of the amino acid sequence set forth in SEQ ID NO: 1. In one embodiment, a mutation site is determined according to a homology alignment software; for example, compared to SEQ ID NO: 1, a sequence has substitutions or deletions at sites other than a specified mutation site X, but the homology alignment software maps the mutated amino acid residue onto site X of SEQ ID NO: 1, and then the sequence still corresponds to the sequence of SEQ ID NO: 1 with a mutation occurring at site X.

In a specific embodiment, the homology or sequence identity may be no less than 90%, preferably no less than 95%, more preferably no less than 98%. The mutation site and a substitution thereof are represented herein by the site number of the mutation site and the amino acid type at the site; for example, S36N indicates that serine corresponding to site 36 of SEQ ID NO:1 is substituted with asparagine in the alignment with SEQ ID NO: 1. In the present invention, "/" is used to indicate a combination of mutation sites; for example, "Y44/F157" indicates a double mutant in which both tyrosine at site 44 and phenylalanine at site 157 are mutated and thus two mutation sites are comprised. Similarly, "F157/C1654196" indicates a triple mutant in which the three corresponding sites are mutated simultaneously.

Herein, the terms "allulose" and "D-allulose", as well as the terms "fructose" and "D-fructose", have the same meaning and are used interchangeably.

The technical solutions of the present invention will be further illustrated in detail with reference to the following specific examples. It should be understood that the following examples are merely exemplary illustration and explanation of the present invention, and should not be construed as limiting the protection scope of the present invention. All techniques implemented based on the aforementioned contents of the present invention are encompassed within the protection scope of the present invention.

Unless otherwise specified, the starting materials and reagents used in the following examples are all commercially available products or can be prepared by known methods.

All macroporous resins conventionally used in the art can be used for the present invention, and the macroporous resins described in the examples are epoxy macroporous resins or amino macroporous resins. The macroporous resin may be self-produced or commercially available, and may be, for example, at least one of ES-1, ES-103, ES-108, ESR-1, ESR-2 and ESQ-1 purchased from Tianjin Nankai Hecheng Science & Technology Co., Ltd, or LX-1000HA, LX-1000EPN and LX-1000EPHA purchased from Xi'an Sunresin Co., Ltd. In practical applications, it is not limited to these resins, and can be purchased from other companies or self-produced, as long as it has the same or similar adsorption capacity to the above resins.

Example 1. Constructing a High-Throughput Screening Method for Mutants

Firstly, RDPE was expressed by *E. coli* as an intracellular enzyme, and the cells were to be crushed; the supernatant obtained after the crushing was used as crude enzyme extract, to which a substrate was added to start a reaction. In order to improve the efficiency, the catalysis can be performed by means of a whole-cell reaction. Besides, the inventor of the present invention have found that a degree of basal expression of the RDPE gene occurs in *E. coli* BL21 host cells and the protein expression level obtained without adding IPTG have already met the requirements for determination of enzyme activity. Therefore, the step of adding IPTG for induction can be omitted.

Secondly, the reaction catalyzed by RDPE is a reversible conversion reaction between fructose and allulose. The enzyme activity can be calculated only by high performance liquid chromatography, which requires considerable time to detect and thus is not suitable for high-throughput screening. Therefore, ribitol dehydrogenase from *Klebsiella* oxide (KRDH) and the coenzyme NADH were added to the whole-cell conversion reaction liquid to start a second round of reaction. Since KRDH has a reducing effect on allulose but not on fructose and NADH is converted into $NAD^+$ in the reaction process, the amount of allulose generated from the conversion of fructose by catalysis of RDPE in the first round of reaction can be determined by detecting changes in absorbance of the reaction liquid at 340 nm. The more obvious the decrease in absorbance is, the more the amount of D-allulose generated is.

Based on the two aspects above, the present invention develops a strategy for efficiently screening an RDPE mutant library by enzyme-linked reaction, optimizes conditions such as reaction mode, determination mode and reaction temperature and finally achieves high-throughput screening of mutants of allulose 3-epimerase or tagatose 3-epimerase. A schematic diagram of the process is shown in FIG. 1. Specifically, the method comprises the following steps:

(1) A transformant was selected from a mutant library and plated on to a 96-well deep-well plate to be cultured at 37° C. and 600 rpm for 16 h, the used medium being an LB medium containing 100 μg/mL ampicillin;

(2) The culture was centrifuged and the supernatant was discarded. 100 μL of 100 mM pH 7.5 potassium phosphate buffer was added to the residue to resuspend the cells, followed by addition of 1% fructose solution to react at 50° C. and 300 rpm for 1 h;

(3) The reaction system was centrifuged and 100 μL of the supernatant was added to a 96-well plate, followed by addition of 100 μL of 50 mM pH 7.5 potassium phosphate buffer containing 10 U KRDH and 2 mM NADH. The resultant mixture was well mixed; and (4) The 96-well plate was subjected to kinetic assay in a microplate reader at a temperature of 30° C. and 340 nm. The more dramatic the decrease in absorbance was, the more the amount of D-allulose in the solution was, indirectly indicating higher enzyme activity of RDPE.

Example 2. Improvement in Enzyme Activity of RDPE by Site Saturation Mutagenesis and Combinatorial Mutagenesis

*Ruminococcus* sp.-derived allulose epimerase (RDPE) was aligned by homology with the amino acid sequences of allulose epimerase and tagatose epimerase reported in the Genbank database. Meanwhile, structure prediction was performed on RDPE. Homology modeling was performed on a wild-type protein of the enzyme by using a software such as Swiss-Model, Phyre2 and Discovery Studio, and molecular docking was performed with fructose molecules used as the substrate so as to predict the catalytic sites and the substrate binding sites of the wild-type enzyme. Besides, the role of the amino acid residues near the sites was analyzed, thereby designing the amino acid sequence of the RDPE mutant. According to the above analysis, sites corresponding to sites S36, G38, Y44, L110, D117, F122, F157, C165, D194, I196, L207, G215, V244, Q251 and I265 of SEQ ID NO.1 were selected as mutation sites to be mutated by saturation mutagenesis so as to establish a single-site saturation mutagenesis library.

Then, transformants in the mutant library were screened by using the high-throughput screening strategy in Example 1. Out of more than 3000 transformants, 8 mutants with 1.2 times improvement in the enzyme activity were obtained by the screening and then sequenced. After sequence analysis, strains expressing corresponding mutants were cultured and induced by adding 0.1 mM IPTG. The mutant proteins were then purified by using Ni column, and the mutants with improved enzyme activity were further re-screened by high performance liquid chromatography. Specifically, the method comprises the following steps:

To an 8% fructose substrate (potassium phosphate buffer, pH 8.0, containing 1 mM $Mn^{2+}$) were added an RDPE wild type and a mutant pure enzyme with appropriate concentrations to react at 60° C. for 20 min. After the reaction was completed, the reaction system was treated in a boiling water bath for 5 min. The content of the product D-allulose was determined by HPLC, and thus the specific enzyme activity of the RDPE wild type and the mutant was calculated. The results are shown in Table 1.

TABLE 1

| Specific enzyme activity of RDPE wild type and single mutants | | |
| --- | --- | --- |
| RDPE wild type or mutants | Specific enzyme activity (U/mg) | Relative enzyme activity (%) |
| WT | 406.63 | 100.00 |
| S36N | 513.26 | 126.22 |
| Y44A | 533.23 | 131.13 |
| D117H | 554.58 | 136.38 |
| F157Y | 556.52 | 136.86 |
| C165A | 551.09 | 135.53 |
| I196F | 561.40 | 138.06 |
| Q251T | 508.37 | 125.02 |
| I265L | 516.61 | 127.05 |

The 8 sites were pairwise combined, resulting in 28 double mutant-expressing strains constructed. The mutant proteins were purified and assayed for activity by HPLC. The results show that the enzyme activity of 21 double mutants was significantly reduced compared to that of the single mutants in the first round of reaction, while the enzyme activity of F157Y/C165A in the remaining seven mutants was significantly improved, the relative enzyme activity thereof being 1.53 times as high as that of the wild type. The specific results are shown in Table 2.

TABLE 2

| Specific enzyme activity of RDPE wild type and single mutants | | |
| --- | --- | --- |
| RDPE wild type or mutants | Specific enzyme activity (U/mg) | Relative enzyme activity (%) |
| WT | 406.63 | 100.00 |
| Y44A/F157Y | 527.97 | 129.84 |
| Y44A/I196F | 551.25 | 135.57 |
| D117H/I196F | 539.54 | 132.69 |
| F157Y/C165A | 623.62 | 153.36 |
| F157Y/Q251T | 574.41 | 141.26 |
| F157Y/I265L | 611.09 | 150.28 |
| I196F/Q251T | 530.60 | 130.48 |

The double mutant F157Y/C165A with the most significantly improved enzyme activity was separately combined with S36N, Y44A, D117H, I196F, Q251T and I265L to construct 6 triple mutants, and mutant proteins were purified and assayed for activity by HPLC. The enzyme activity is shown in Table 3. It can be seen that the enzyme activity of the triple mutant F157Y/C165A/S36N was significantly reduced, while the enzyme activity of F157Y/C165A/I196F and F157Y/C165A/Q251T was significantly improved compared to that of the wild type and was more significantly improved than that of the double mutant F157Y/C165A.

TABLE 3

Specific enzyme activity of RDPE wild type and triple mutants

| RDPE wild type or mutants | Specific enzyme activity (U/mg) | Relative enzyme activity (%) |
|---|---|---|
| WT | 406.63 | 100.00 |
| F157Y/C165A/S36N | 277.72 | 68.30 |
| F157Y/C165A/Y44A | 497.18 | 122.27 |
| F157Y/C165A/D117H | 439.06 | 107.98 |
| F157Y/C165A/I196F | 699.71 | 172.08 |
| F157Y/C165A/Q251T | 677.13 | 166.73 |
| F157Y/C165A/I265L | 480.90 | 118.26 |

Example 3. Improvement in Stability of RDPE by Site Saturation Mutagenesis and Combinatorial Mutagenesis Mutants (I196F, F157Y/C165A, F157Y/I265L, F157Y/C165A/I196F and F157Y/C165A/Q251T) with relative enzyme activity of more than 150% were selected from RDPE single mutants, double mutants and triple mutants and assayed for thermostability. The specific assay method comprises the following steps: RDPE mutants were subjected to heat treatment at 60° C. for 30 min, 60 min, 120 min and 240 min and were assayed for enzyme activity with fructose used as the substrate. The enzyme activity of the mutants not subjected to heat treatment was defined as 100%, and the residual enzyme activity after heat treatment was calculated. The results are shown in Table 4, and it can be seen that the thermostability of the selected five mutants are improved to a certain degree compared to that of the wild type, wherein the thermostability of the triple mutant F157Y/C165A/I196F was most significantly improved.

TABLE 4

Comparison of thermostability of RDPE wild type and mutants

| RDPE wild type or mutants | Residual enzyme activity (%) | |
| | 120 min of heat treatment | 240 min of heat treatment |
|---|---|---|
| WT | 68.11 | 34.17 |
| I196F | 68.26 | 44.27 |
| F157Y/C165A | 87.34 | 74.79 |
| F157Y/I265L | 79.84 | 52.80 |
| F157Y/C165A/I196F | 92.02 | 83.77 |
| F157Y/C165A/Q251T | 82.97 | 61.71 |

Figure 2:
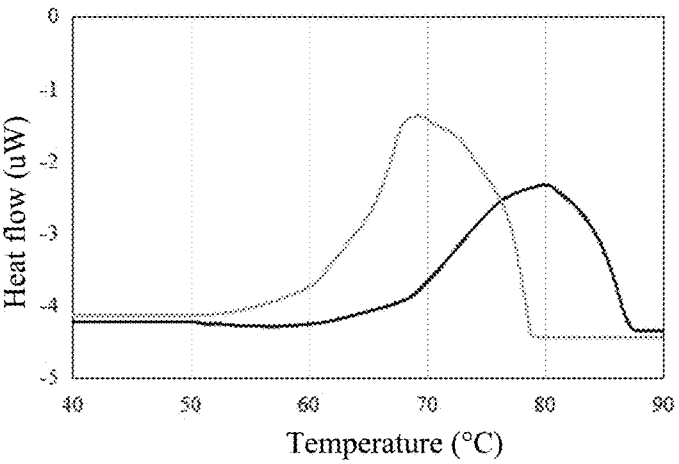
FIG. 2 shows the determined melting temperatures (Tm) of an RDPE mutant and an RDPE wild type.

The melting temperatures (Tm) of proteins of the RDPE wild type and the RDPE triple mutant F157Y/C165A/I196F with the most significantly improved enzyme activity and stability were further determined by differential scanning calorimetry, and the results are shown in FIG. 2. The results show that the Tm values of the RDPE wild type and the RDPE triple mutant F157Y/C165A/I196F were 69.3° C. and 79.9° C., respectively. The significant increase in Tm indicates that the thermostability of the RDPE mutant was significantly improved compared to that of the RDPE wild type.

Figure 3:
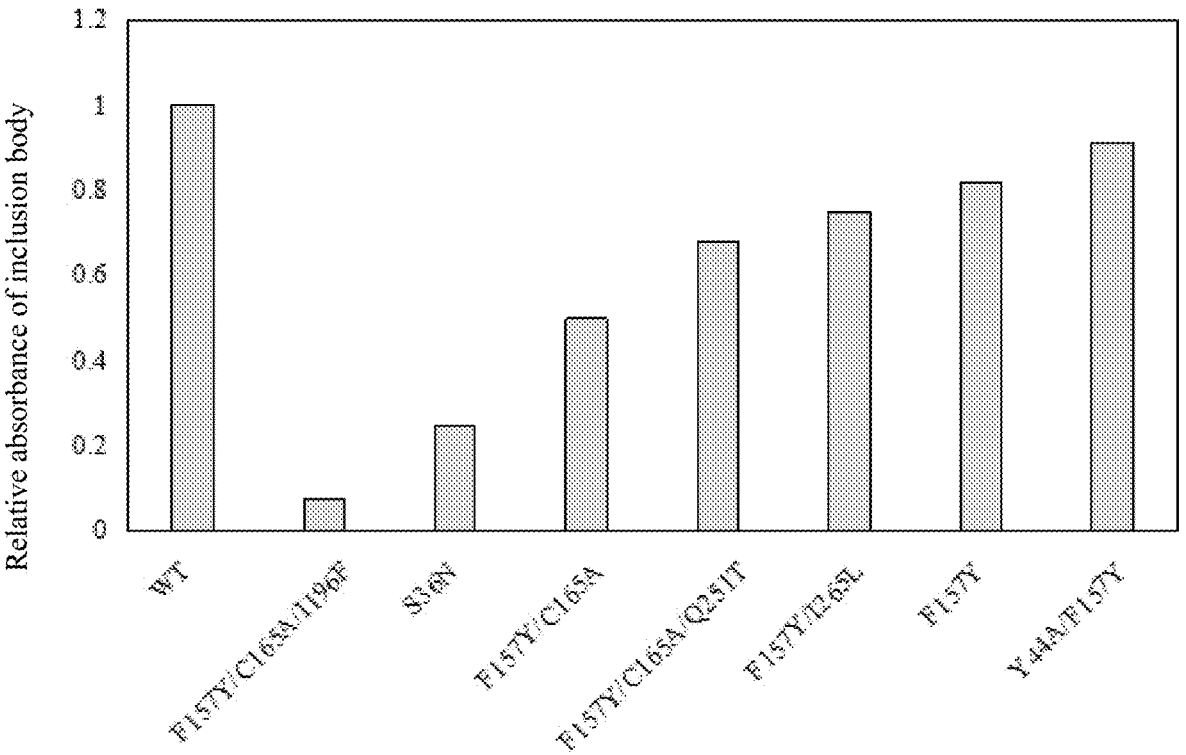
FIG. 3 shows the comparison of the amount of the inclusion bodies heterologously expressed by an RDPE mutant and an RDPE wild type in *E. coli;*

Example 4. Increase in Soluble Expression Level of RDPE in E. coli by Site-Directed Mutagenesis In the above examples, the expression of all of the RDPE mutants was performed in E. coli BL21. As the previous experiments found that the expression of the RDPE wild type in E. coli would result in inclusion bodies, the expression was induced at low temperature and low rotation speed (20° C., 100 rpm). It was found in experiments that the amount of the generated protein inclusion bodies was significantly affected by mutations at different sites, wherein the amount of the generated protein inclusion bodies of mutants S36N, F157Y, Y44A/F157Y, F157Y/C165A, F157Y/I265L, F157Y/C165A/I196F and F157Y/C165A/Q251T was reduced compared to that of the wild type, while the amount of the generated protein inclusion bodies of the other mutants was increased compared to that of the wild type. In order to determine the quantity of the generated inclusion bodies, the suspension obtained after ultrasonic crushing was properly diluted with water and assayed for absorbance at 600 nm with the absorbance of the RDPE wild type at 600 nm defined as 1. The relative value of the absorbance of each mutant was calculated, and the turbidity was used as a quantitative index to the amount of the generated inclusion bodies. FIG. 3 shows the relative value of the absorbance of each mutant with a reduced amount of the generated inclusion bodies. It can be seen that when the triple mutant F157Y/C165A/I196F was expressed in E. coli, the amount of the generated inclusion bodies was significantly reduced, so that the soluble protein level could be improved. A further attempt to increase the temperature of the induced expression of the mutant to 25° C. still resulted in a very small generation amount of the inclusion bodies. The reduction in the generation of inclusion bodies is beneficial to enabling more proteins to express into active soluble forms and improves the efficiency and yield of producing the RDPE enzyme in E. coli by fermentation. Therefore, the mutants have a great application prospect.

Example 5. Increase in Secretory Expression Level of RDPE in B. subtilis by Site-Directed Mutagenesis Since RDPE can be secreted and expressed in B. subtilis, the secretory expression levels of mutants F157Y/C165A, F157Y/I265L, F157Y/C165A/I196F and F157Y/C165A/Q251T in B. subtilis were further analyzed. With pMA5 used as the vector and B. subtilis 168 used as host bacteria, the engineered strains B-0, B-1, B-2, B-3 and B-4 expressing the RDPE wild type and mutants are constructed and cultured in SR medium for 48 h. The RDPE secreted into the fermentation broth was assayed for enzyme activity. The results are shown in Table 5, and it can be seen that the secretory expression levels of the selected RDPE mutants in B. subtilis were significantly increased compared to that of the wild type.

TABLE 5

Secretory expression levels of RDPE mutants and wild type in B. subtilis

| Strains | Corresponding RDPE genotypes | Enzyme activity of supernatant after fermentation (U/mL) | Concentrations of corresponding proteins (g/L) |
|---|---|---|---|
| B-0 | WT | 421.06 | 1.04 |
| B-1 | F157Y/C165A | 894.41 | 1.43 |
| B-2 | F157Y/I265L | 778.60 | 1.27 |
| B-3 | F157Y/C165A/I196F | 988.34 | 1.41 |
| B-4 | F157Y/C165A/Q251T | 846.05 | 1.25 |

Figure 4:
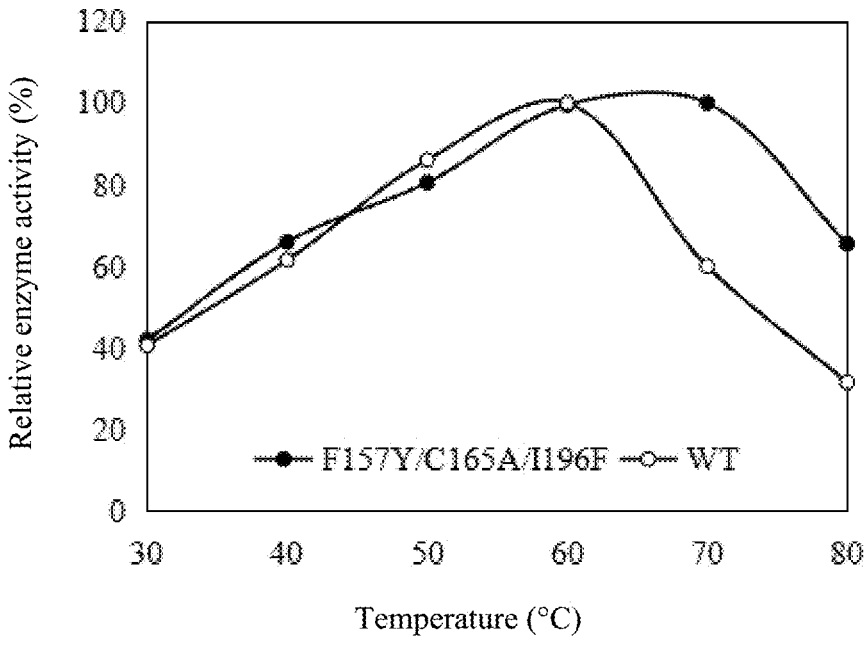
FIG. 4 shows the comparison of the relative enzyme activity of an RDPE mutant F157Y/C165A/I196F and an RDPE wild type at different temperatures (30, 40, 50, 60, 70 and 80° C.)

Example 6. Increase in Optimal Reaction Temperature and Fructose Conversion Rate of RDPE by Site-Directed Mutagenesis The enzyme activity of the RDPE wild type and the RDPE mutant F157Y/C165A/I196F at different temperatures (30, 40, 50, 60, 70 and 80° C.) was determined. The relative enzyme activity was calculated with the highest enzyme activity defined as 100%, and the influence of temperature on enzyme activity was investigated, as shown in FIG. 4. It can be seen that the optimal temperature for the mutant F157Y/C165A/I196F was increased from 60° C. to 70° C., and no less than 65% of the relative enzyme activity was retained at 80° C., while only about 30% of the relative enzyme activity of the wild type was retained at 80° C.

With 50% fructose used as the substrate, the RDPE wild type and the RDPE mutants F157Y/C165A, F157Y/I265L, F157Y/C165A/I196F and F157Y/C165A/Q251T were added at 20 U per gram of fructose to start conversion reactions at 60° C., 70° C. and 80° C., and the equilibrium conversion rates were determined. The results are shown in Table 6. The result shows that the wild type RDPE had poor thermostability, and the conversion rate decreased with the increasing temperature; the conversion rates of the 4 mutants tested were significantly improved compared to that of the wild type, and gradually increased with the increasing temperature up to about 33%. Therefore, the mutants have a great industrial application prospect.

TABLE 6

Catalytic efficiency for fructose at different temperatures by RDPE mutants and wild type

| RDPE wild type and mutants | Conversion rates at 60° C. (%) | Conversion rates at 70° C. (%) | Conversion rates at 80° C. (%) |
|---|---|---|---|
| WT | 26.3 | 25.6 | 24.8 |
| F157Y/C165A | 28.6 | 30.1 | 32.5 |
| F157Y/I265L | 28.2 | 29.8 | 31.8 |
| F157Y/C165A/I196F | 30.4 | 31.9 | 33.5 |
| F157Y/C165A/Q251T | 27.9 | 29.5 | 31.2 |

Example 7. Construction of Engineered Secretory *B. subtilis* Strain

In order to further improve the secretory expression level of the RDPE mutant F157Y/C165A/I196F in *B. subtilis*, with *B. subtilis* 168 used as the host bacterium, an engineered stain B-3-1 expressing the RDPE mutant F157Y/C165A/I196F was constructed by using a *B. subtilis* expression vector pNWP43N containing a constitutive expression promoter P43. Specifically, the method comprises the following steps: the gene segment of the RDPE mutant F157Y/C165A/I196F was amplified by PCR and linked to the vector by enzyme digestion; the ligation product was added to *B. subtilis* 168 competence, well mixed and recovered at 37° C. and 200 rpm for 1.5 h; all of the mixed solution was applied to an LB plate containing chloramphenicol (25 μg/mL) and verified by colony PCR. Thus, the engineered secretory *B. subtilis* strain B-3-1 was obtained.

Example 8. Enzyme Production of *B. subtilis* by Fermentation

Figure 5:
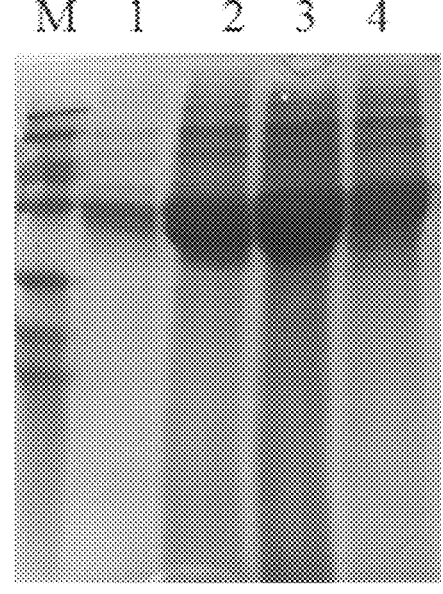
FIG. 5 shows the expression of an RDPE mutant in an engineered *B. subtilis* strain B-3-1 (M: protein molecular weight standard, 1: supernatant after 18 h of fermentation, 2: supernatant after 24 h of fermentation, 3: supernatant after 30 h of fermentation, and 4: supernatant after 42 h of fermentation)

By optimizing conditions for fermentation, fermentation with the engineered strain B-3-1 was performed in a 5 L fermentor at 37° C. and 300 rpm for 48 h with SR medium used. The RDPE activity in the fermentation broth was determined to reach 1436 U/mL. The results show that the mutant plasmid of the present invention has greatly improved stability, thereby resulting in an improved secretory expression level of the heterologous protein RDPE. Meanwhile, the RDPE mutant secreted into the medium was detected by SDS-PAGE (FIG. 5), and the results show that the target protein was extensively secreted and expressed into the fermentation medium with less host protein impurities contained.

Example 9. Immobilization Method for Allulose 3-Epimerase 200 g of a resin (ES-1, ES-103, ES-108, ESR-1, ESR-2 or ESQ-1) was weighted and activated in 2 L of a PBS buffer (22.8 g of dipotassium hydrogenphosphate and 2.75 g of potassium dihydrogenphosphate, made up to a total volume of 1000 mL, about pH 7.5). The mixture was appropriately stirred for about 2 h and filtered to obtain an activated resin.

The allulose 3-epimerase was derived from *Ruminococcus* sp. and had an amino acid sequence set forth in SEQ ID NO: 1. An extracellular enzyme was produced by fermentation with *B. subtilis* B-0, and the fermentation broth was centrifuged to collect the supernatant for use as a crude enzyme extract. The crude enzyme extract of allulose 3-epimerase was added with an activated resin with proper weight and stirred at room temperature overnight for immobilization. Then, the immobilized enzyme was crosslinked with a 0.4% glutaraldehyde solution, washed and drained to obtain the immobilized enzyme of allulose 3-epimerase. Allulose 3-epimerase was immobilized by using different resins, and the activity of the immobilized enzymes is shown in Table 7. The results show that allulose 3-epimerase can be well immobilized by using different types of macroporous resins from Tianjin Nankai Hecheng Science & Technology Co., Ltd, wherein the epoxy resin ES-108-immobilized enzyme has the highest enzyme activity.

TABLE 7

Activity of immobilized enzymes obtained by using different resins

| Resins | Activity of immobilized enzymes (U/g) |
|---|---|
| ES-1 | 320.83 |
| ES-103 | 411.03 |
| ES-108 | 438.69 |
| ESR-1 | 341.13 |
| ESR-2 | 365.18 |
| ESQ-1 | 322.20 |

Example 10. Improvement in Immobilization Efficiency and Thermostability of Allulose 3-Epimerase In order to further improve the immobilization efficiency of allulose 3-epimerase and enhance the binding of the enzyme to the resin carrier, an AKAKAKAKAK tag was added to a carboxyl terminal of allulose 3-epimerase (namely, modified enzyme). The amino group on the side chain of the basic amino acid (lysine) on the tag serves as an additional site of the enzyme for binding to epoxy groups on resins, thereby improving the immobilization efficiency. The experimental results show that the immobilization efficiency of ES-108 resin for untagged allulose 3-epimerase was 74.7%, while the immobilization efficiency of ES-108 resin for the AKAKAKAKAK-tagged allulose 3-epimerase reached 100%. The experimental results also show that allulose 3-epimerase did not show a noticeable change in the specific enzyme activity after being tagged.

Figure 6:
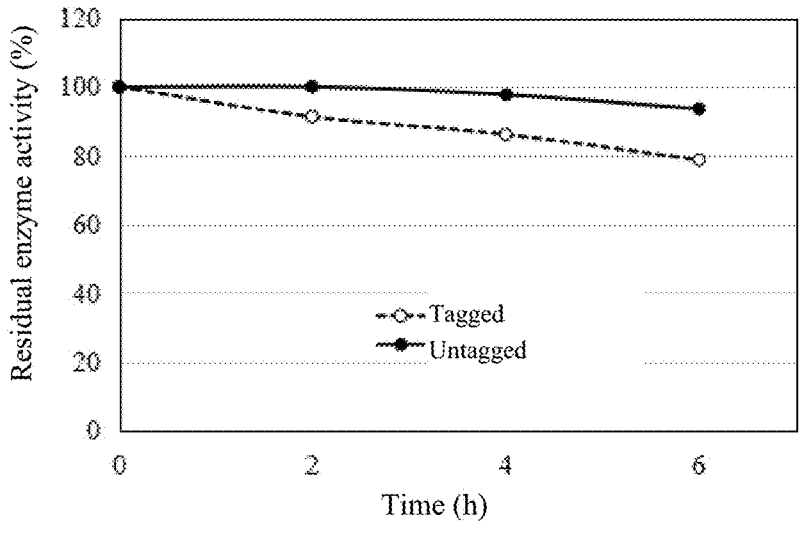
FIG. 6 shows the improvement in the thermostability of an immobilized enzyme of allulose 3-epimerase by addition of a tag.

The thermostability of the immobilized enzymes of the tagged and untagged allulose 3-epimerase was determined at 60° C.; specifically, the immobilized enzymes were incubated at 60° C. for a certain period of time and then added to fructose solution to determine the enzyme activity, and the residual enzyme activity of the immobilized enzymes after the incubation was calculated with the enzyme activity of the immobilized enzyme not incubated defined as 100%. The results are shown in FIG. 6, and it can be seen that the immobilized enzyme of the tagged allulose 3-epimerase has significantly improved thermostability compared to the untagged immobilized enzyme, with no less than 90% of the activity retained after 6 h of incubation at 60° C. The half-lives of the immobilized enzymes were calculated. The tagged immobilized enzyme had a half-life of 47.9 h at 60° C., while the untagged immobilized enzyme had a half-life of only 14.4 h at 60° C. The results show that the addition of the tag can facilitate the significant improvement in the thermostability of the immobilized enzyme. The application of the tagged immobilized enzyme of allulose 3-epimerase was studied to determine its effects in batch reactions and continuous reactions.

Example 11. Reusability of Immobilized Enzyme of Allulose 3-Epimerase

Figure 7:
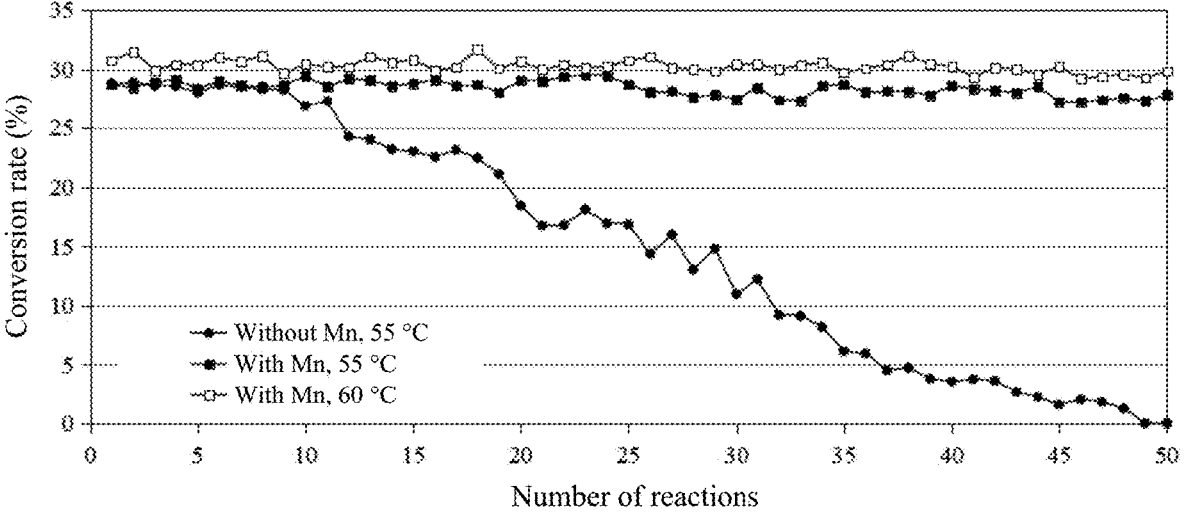
FIG. 7 shows the reusability of an immobilized enzyme of allulose 3-epimerase.

The reusability of the immobilized enzyme was determined by batch reactions. To a 50% (w/v) fructose solution substrate was added the 10% (w/w) modified immobilized enzyme of which a carboxyl terminal was added with an AKAKAKAKAK tag according to Example 10. After 2 h of reaction at a temperature of 55° C., the reaction system was sampled to determine the conversion rate and then filtered to obtain the immobilized enzyme, which was added to a fresh 50% (w/v) fructose solution to start a second round of reaction. After 2 h of reaction, the reaction system was sampled to determine the conversion rate. The above procedure was repeated until no less than 50 rounds of reaction were completed. The results are shown in FIG. 7, and it can be seen that the immobilized enzyme of allulose 3-epimerase added at this amount could catalyze the epimerization reaction to reach the equilibrium within 2 h, with the conversion rate being about 30%; besides, $Mn^{2+}$ added to the reaction system was found to significantly improve the stability of the immobilized enzyme of allulose 3-epimerase; the reaction was repeated 50 times, with the conversion rate for fructose to allulose being 28-29%.

Example 12. Reusability of Immobilized Enzyme of Allulose 3-Epimerase

This example was modified from Example 11 so as to further increase the conversion rate and shorten the time required for the reaction.

The reusability of the immobilized enzyme was determined by batch reactions. To a 50% (w/v) fructose solution substrate was added the 10% (w/w) modified immobilized enzyme of which a carboxyl terminal was added with an AKAKAKAKAK tag according to Example 10. After 1 h of reaction at a temperature of 60° C., the reaction system was sampled to determine the conversion rate, followed by remaining procedures as in Example 11. The results show that the immobilized enzyme of allulose 3-epimerase added at this amount could catalyze the epimerization reaction to reach the equilibrium within 1 h, with the conversion rate exceeding 30%; the reaction was repeated 50 times, with conversion rate for fructose to allulose being 30-31%.

Example 13. Reusability of Immobilized Enzyme of Allulose 3-Epimerase

This example was modified from Example 11 so as to reduce the amount of enzyme required, to improve the reusability of the immobilized enzyme and thus to reduce the cost.

The reusability of the immobilized enzyme was determined by batch reactions. To a 50% (w/v) fructose solution substrate was added the 5% (w/w) modified immobilized enzyme of which a carboxyl terminal was added with an AKAKAKAKAK tag according to Example 10. After 4 h of reaction at a temperature of 50° C., the reaction system was sampled to determine the conversion rate, followed by remaining procedures as in Example 11. The results show that the immobilized enzyme of allulose 3-epimerase added at this amount could catalyze the epimerization reaction to reach the equilibrium within 4 h; the reaction was repeated up to 80 times, with the conversion rate for fructose to allulose by the immobilized enzyme being 27-28%.

Example 14. Reusability of Immobilized Enzyme of Allulose 3-Epimerase

This example was modified from Example 13 so as to further improve the reusability of the immobilized enzyme and reduce reaction energy consumption by lowering the reaction temperature.

The reusability of the immobilized enzyme was determined by batch reactions. To a 50% (w/v) fructose solution substrate was added the 5% (w/w) modified immobilized enzyme of which a carboxyl terminal was added with an AKAKAKAKAK tag according to Example 10. After 4 h of reaction at 40° C., the reaction system was sampled to determine the conversion rate, followed by remaining procedures as in Example 13. The results show that the immobilized enzyme of allulose 3-epimerase added at this amount could catalyze the epimerization reaction to reach the equilibrium within 4 h; the reaction was repeated up to 100 times, with the conversion rate for fructose to allulose by the immobilized enzyme being 26-27%.

Example 15. Continuous Production of Allulose by Immobilized Enzyme Reactor of Allulose 3-epimerase A column (φ26×200) with a heat-retaining jacket was filled with the modified immobilized enzyme of which a carboxyl terminal was added with an AKAKAKAKAK tag according to Example 10 to be used as an immobilized enzyme reactor. By the optimization of reaction conditions and parameters, it was found that when the temperature of the heat-retaining jacket was controlled at 50° C. and a 70% (w/v) fructose solution (containing 1 mM $Mn^{2+}$) was passed through the immobilization reactor at 2.5 mL/min, the ratio of allulose to fructose in the fluid flowing out of the reactor is basically in equilibrium, with the equilibrium conversion rate being 28-29%, and the immobilization reactor had a half-life of no less than 100 days.

Example 16. Immobilization of RDPE Mutant Enzyme

A suitable immobilization resin was selected to directly immobilize the RDPE mutant crude enzyme extract produced by fermentation with the engineered secretory *B. subtilis* strain B-3-1 constructed in Example 7.

200 g of a resin (LX-1000HA, LX-1000EPN or LX-1000EPHA) was weighted and activated in 2 L PBS buffer (22.8 g of dipotassium hydrogenphosphate and 2.75 g of potassium dihydrogenphosphate, made up to a total volume of 1000 mL, about pH 7.5). The mixture was appropriately stirred for about 2 h and filtered to obtain an activated resin. The 10% (w/v) activated resin was then added to the fermented crude enzyme extract of engineered secretory *B. subtilis* strain B-3-1 capable of producing RDPE mutant enzymes. The mixture was stirred at room temperature overnight for immobilization and filtered to separate the immobilized enzyme and supernatant waste. The supernatant waste was assayed for DPE activity, and the results show that almost no DPE activity was detected in the waste, indicating that the free RDPE can be completely immobilized on these 3 resins, with the immobilization efficiency being 100% (fermented crude enzyme extract not added with immobilization resins was left standing at room temperature overnight as a control, and the DPE activity was barely changed). The immobilized enzyme was finally crosslinked with a 0.4% glutaraldehyde solution, washed and drained to obtain the immobilized enzyme.

Figure 8:
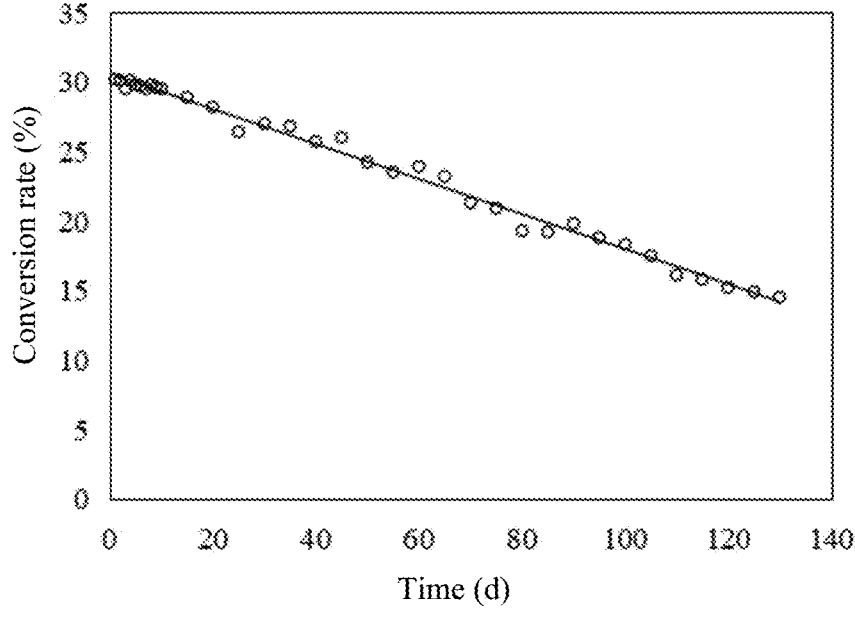
FIG. 8 shows the conversion rate over time for the immobilized enzyme reactor in Example 9.

A column ($\varphi 26 \times 200$) with a heat-retaining jacket was filled with the immobilized enzyme obtained by immobilization of the RDPE mutant enzyme by LX-1000EPHA to be used as an immobilized enzyme reactor. Allulose was produced by using the immobilization reactor. A 500 g/L fructose solution (containing 1 mM $Mn^{2+}$) was passed through the immobilization reactor at 240 mL/h with the reaction temperature controlled at 55° C., and the fluid flowing out was sampled at regular intervals to determine the conversion rate for allulose. The results are shown in FIG. 8, and it can be seen that the maximum conversion rate for allulose reached no less than 30% and the immobilization reactor had a half-life of about 125 days.

The embodiments of the present invention have been described above. However, the present invention is not limited to the above embodiments. Any modifications, equivalents, improvement and the like made without departing from the spirit and principle of the present invention shall fall within the protection scope of the present invention.

---

The invention claimed is:

1. An allulose 3-epimerase mutant, comprising an amino acid sequence of at least 98.6% identity to SEQ ID NO: 1, and a combination of point mutations selected from the group consisting of:

i) Y44A and F157Y;
ii) F157Y and C165A;
iii) F157Y, C165A, and S36N;
iv) F157Y, C165A, and Y44A;
v) F157Y, C165A, and D117H;
vi) F157Y, C165A, and I196F;
vii) F157Y, C165A, and Q251T;
viii) F157Y, C165A, and I265L; and
ix) F157Y and I265L.

2. A nucleic acid encoding the allulose 3-epimerase mutant according to claim 1.

3. A genetically engineered bacterium expressing an allulose 3-epimerase mutant, comprising the nucleic acid encoding the allulose 3-epimerase mutant according to claim 2.

4. A method for making a genetically engineered bacterium, comprising linking the nucleic acid according to claim 2 to a vector to obtain a recombinant vector, and then introducing the recombinant vector into a host bacterium.

5. A method for preparing an allulose 3-epimerase mutant, comprising culturing the genetically engineered bacterium according to claim 3.

6. A production method for D-allulose, comprising contacting the allulose 3-epimerase mutant according to claim 1 with fructose.

7. The allulose 3-epimerase mutant according to claim 1, further comprising a lysine-rich tag, is added to the carboxyl-terminus of the amino acid sequence.

8. A method for preparing an immobilized allulose 3-epimerase mutant, comprising:

(1) resin activation: activating a macroporous resin in a buffer;
(2) preparation of enzyme: preparing an enzyme extract by fermentation with the genetically engineered bacterium expressing an allulose 3-epimerase mutant according to claim 3;
(3) immobilization: mixing the activated resin from step (1) with the enzyme extract of step (2); and
(4) crosslinking: adding a crosslinking reagent to the mixture from step (3).

9. An immobilized enzyme of allulose 3-epimerase, consisting of the allulose 3-epimerase mutant according to claim 1 and a resin.

10. An immobilized enzyme of allulose 3-epimerase, consisting of the allulose 3-epimerase mutant according to claim 7 and a resin.

11. The preparation method according to claim 8, wherein, in step (1), the resin is an epoxy macroporous resin or an amino macroporous resin, and/or the buffer is a potassium phosphate buffer with a pH of 7.5-8.0.

12. The preparation method according to claim 8, wherein the immobilization in step (3) is performed at a temperature of 20-40° C. for a duration of 12-24 h.

* * * * *